United States Patent
Fujita et al.

(10) Patent No.: US 6,337,006 B1
(45) Date of Patent: Jan. 8, 2002

(54) LANTHANUM GALLATE SINTERED BODY

(75) Inventors: Hiroki Fujita, Aichi; Ryuji Inoue, Gifu; Takafumi Oshima, Aichi, all of (JP)

(73) Assignee: NGK Spark Plug Co., Ltd., Aichi (JP)

( * ) Notice: Subject to any disclaimer, the term of this patent is extended or adjusted under 35 U.S.C. 154(b) by 0 days.

(21) Appl. No.: 09/499,359

(22) Filed: Feb. 8, 2000

(30) Foreign Application Priority Data

Feb. 8, 1999 (JP) ............................................ 11-030661
Apr. 8, 1999 (JP) ............................................ 11-100752
Jun. 7, 1999 (JP) ............................................ 11-159512

(51) Int. Cl.[7] ........................ G01N 27/406; C04B 35/01
(52) U.S. Cl. ........................ 204/421; 204/424; 501/152
(58) Field of Search ................ 204/424–429, 204/421; 429/30, 33; 501/152; 252/521.1, 62.2

(56) References Cited

U.S. PATENT DOCUMENTS

| 4,935,934 A | * | 6/1990 | Ferrand et al. ................ 372/41 |
| 4,944,833 A | * | 7/1990 | Belt et al. ...................... 117/13 |
| 5,234,722 A | * | 8/1993 | Ito et al. ......................... 429/33 |
| 6,004,688 A | * | 12/1999 | Goodenough et al. ........ 429/33 |

FOREIGN PATENT DOCUMENTS

| EP | 0 276 519 | 8/1988 |
| EP | 0 797 094 A2 | 9/1997 |
| JP | 9-161824 | 6/1997 |
| JP | 9-311120 | 12/1997 |

OTHER PUBLICATIONS

Nguyen et al., "Electrical conductivity, thermal expansion and reaction of (La, Sr)(Ga,Mg)O3 and (La, Sr)AlO3 system", Solid State Ionics 132, pp. 217–226, 2000 month N/A.*

Huang et al., "Characterization of Sr–doped LaMnO3 and LaCoO3 as Cathode Materials for a Doped LaGaO3 Ceramic Fuel Cell", J. Electrochem. Soc. 143, pp. 3630–3636, 1996 month N/A.*

K. Yamaji et al., "Compatibility of $LaO_{0.9}Sr_{0.1}G_{0.8}Mg_{0.2}O_{2.85}$ as the electrolyte for SOFC", Solid State Ionics, vol. 108, No. 1–4, May 1, 1998, pp. 415–421 (XP004119381.

W. Stevenson et al., "Effect of A–site cation stoichiometry on the properties of doped lanthanum gallate", Solid State Ionics, vol. 113–115, Dec. 1998, pp. 571–583 (XP000097806).

K. Choy et al., "The development of intermediate–temperature solid oxide fuel cells for the next millennium"; Journal of Power Sources, vol. 71, No. 1–2, Mar. 15, 1998, pp. 361–369 (XP004112472).

(List continued on next page.)

Primary Examiner—Robert J. Warden, Sr.
Assistant Examiner—Kaj K. Olsen
(74) Attorney, Agent, or Firm—Sughrue Mion, PLLC

(57) ABSTRACT

Disclosed is an $LaGaO_3$ sintered body which comprises lanthanum, gallium, oxygen and at least one of other elements, and has at least three crystal phases of different composition formula.

18 Claims, 11 Drawing Sheets

OTHER PUBLICATIONS

R.T. Baker et al., "Processing and Electrical Conductivity of Pure, Fe– and Cr–subsituted $La_{0.9}Sr_{0.1}GaO_3$", Journal of the European Ceramic Society, vol. 18, No. 2, 1998, pp. 105–112 (XP004101521) month unknown.

E. Djurado et al., "Second Phases in Doped Lanthanum Gallate Perovskites", Journal of the European Ceramic Society, vol. 18, No. 10, Sep. 1, 1998, pp. 1397–1404 (XP004132939).

N.M. Sammes et al., "Charactiersation of doped–lanthanum gallates by X–ray diffraction and Raman spectroscopy", Solid State Ionics, vol. 111, No. 1–2, Aug. 1, 1998, pp. 1–7 (XP004148660).

K. Huang et al., "Superior perovskite oxide–ion conductor; Strontium– and Magnesium doped $LaGaO_3$: I, Phase relationships and electrical properties" Journal of the American Ceramic Society, vol. 81, No. 10, 1998, pp. 2565–2575 (XP002156111) month unknown.

T. Ishihara et al., "Doped $LaGaO_3$ perovskite type oxide as a new oxide ionic conductor", Journal of the American Chemical Society, vol. 116, No. 9, 1994, pp. 3801–3803 (XP002156112) month unknown.

* cited by examiner

INVENTIVE
(SAMPLE NO. 1C)

INVENTIVE
(SAMPLE NO. 2C)

COMPARATIVE
(SAMPLE NO. 4C)

LANTHANUM GALLATE SINTERED BODY

BACKGROUND OF THE INVENTION

1. Field of the Invention

This invention relates to an $LaGaO_3$-based sintered body (hereinafter $LaGaO_3$ sintered body). More particularly, it relates to an $LaGaO_3$ sintered body which has high mechanical strength and excellent electrical conductivity and is therefore applicable to practical big-volume products. The $LaGaO_3$ sintered body of the invention is useful as an oxygen-permeable membrane, a reactor, a sensor device, etc.

This invention also relates to an $LaGaO_3$-based sintered body which is suited for use in, for example a sensor device and a process for producing the same.

This invention further relates to a sensor device using an oxide ion-conducting solid electrolyte. More particularly it relates to a critical current sensor device which has improved adhesibility between solid electrolyte and electrode, which has reduced solid electrolyte/electrode interfacial resistance by increasing three-phase interface comprising gas phase, electrode and solid electrolyte between solid electrolyte and electrode, and therefore exhibits improved oxygen pumping ability.

2. Background Art

It is known that an $LaGaO_3$ sintered body is far more electrically conductive than stabilized zirconia and can be used as an electrolyte of a solid electrolyte fuel cell that exhibits excellent power generation properties in a low-temperature range as disclosed in JP-A-9-161824. However, the problem of the $LaGaO_3$ sintered body of the background art is its low mechanical strength. For example, the bending strength of yttrium-stabilized zirconia (hereinafter referred to as YSZ) as obtained by sintering at 1500° C. is 500 MPa, while that of $LaGaO_3$ sintered body is as low as 200 MPa or even lower. Therefore, in order to apply $LaGaO_3$ sintered body to practical products, particularly big-volume products, it has been necessary to add extensive improvements in mechanical strength.

An oxygen sensor device having an oxide ion conductor typically uses stabilized zirconia solid electrolyte as an oxide ion conductor. Such an oxygen sensor device has been used in practice as, for example, an oxygen sensor for automotive engines. Zirconia oxides have also been used in broad fields as fuel cells, reactors, etc. because of their chemical stability and high oxygen conductivity.

The exhaust gas sensor disclosed in JP-A-9-311120 can be mentioned as an example of sensor devices using a zirconia oxide. According to the disclosure, an oxygen pump cell comprising an oxide ion-conducting solid electrolyte is operated in such a manner that an oxygen sensor cell comprising an oxide ion-conducting solid electrolyte which is placed in a detection chamber may give constant signals (the electromotive force of an oxygen concentration cell) and a component of an exhaust gas is detected from a resistivity change of a semiconductor detector placed in the detection chamber.

However, in detecting hydrocarbons (HC) with the above-described sensor device, hydrocarbons tend to react with oxygen and decompose (i.e., the concentration of the component to be detected decreases) by the catalytic action of the noble metal electrodes used in the oxygen pump cell and the oxygen sensor cell, resulting in reduction of detection accuracy. If at least the electrodes of the oxygen pump cell and the oxygen sensor cell that face the detection chamber are made of a material which is catalytically inert to hydrocarbons, hydrocarbons will hardly react and decompose in the detection chamber, whereby accurate detection of hydrocarbons could be achieved.

In order to achieve high oxide ion conduction by use of a zirconia oxide, the working temperature must be as high as 700° C. or even higher because the zirconia oxide itself does not exhibit high oxide ion conductivity at low temperature. Further, the interfacial resistance between the electrodes (e.g., Pt electrodes or Au electrodes) and a zirconia oxide is high due to poor adhesion to each other.

Most of hydrocarbons will be burnt at such a high working temperature as 700° C. or higher and are no more measurable whether or not the electrodes are made of a material catalytically inert to the hydrocarbons. Additionally, considering the sensing system as a whole, high power consumption arising from the high working temperature is problematical.

An $LaGaO_3$ oxide is known as an oxide ion-conducting solid electrolyte that works at lower temperatures than a zirconia oxide. However, it has been pointed out that an $LaGaO_3$ oxide is reactive with a noble metal, particularly Pt, so that a sensor device comprising a Pt electrode in combination with an $LaGaO_3$ oxide has an increased interfacial resistance, failing to perform a high oxygen pumping function. It is necessary to use a noble metal, which is hardly oxidized even in high temperature, as an electrode material in sensor devices used at 500° C. or higher. Hence, the reactivity of an $LaGaO_3$ oxide with a noble metal has been a hindrance to application of this oxide to a sensor device.

Yttrium-stabilized zirconia is known as a solid electrolyte useful in a sensor, etc. and has been used widely. The problem of YSZ used in a sensor is that its oxide ion conductivity drastically reduces in low temperature so that the working temperature of the sensor should be high enough in order to obtain high ion conductivity.

A sintered body of lanthanum-gallium mixed oxide having a perovskite structure, i.e., lanthanum gallate-based sintered body ($LaGaO_3$ sintered body) has recently been attracting attention as a substance showing higher oxide ion conductivity than YSZ and been given much study.

The $LaGaO_3$ sintered body comprises $LaGaO_3$ with part of La or Ga displaced with a less valent atom, such as Sr or Mg, by substitutional solid dissolution to have increased oxide ion conductivity.

However, it is difficult to obtain a dense $LaGaO_3$ sintered body. Even through firing is performed at 1500° C. or even higher temperatures, the resulting sintered body tends to have gathered pores.

SUMMARY OF THE INVENTION

An object of the present invention is to provide an $LaGaO_3$ sintered body having markedly improved mechanical strength without greatly impairing the high electrical conductivity inherent thereto.

An object of the invention is to provide a sensor device which has a markedly reduced interfacial resistance between an oxide ion-conducting solid electrode and a noble metal electrode and therefore exhibits greatly improved oxygen pumping ability and works satisfactorily even in temperatures of 700° C. or lower.

An object of the present invention is to provide a dense $LaGaO_3$ sintered body having a high density and a process for producing the same.

BRIEF DESCRIPTION OF THE DRAWINGS
Brief Description of Drawings

DETAILED DESCRIPTION OF THE INVENTION

Figure 1:
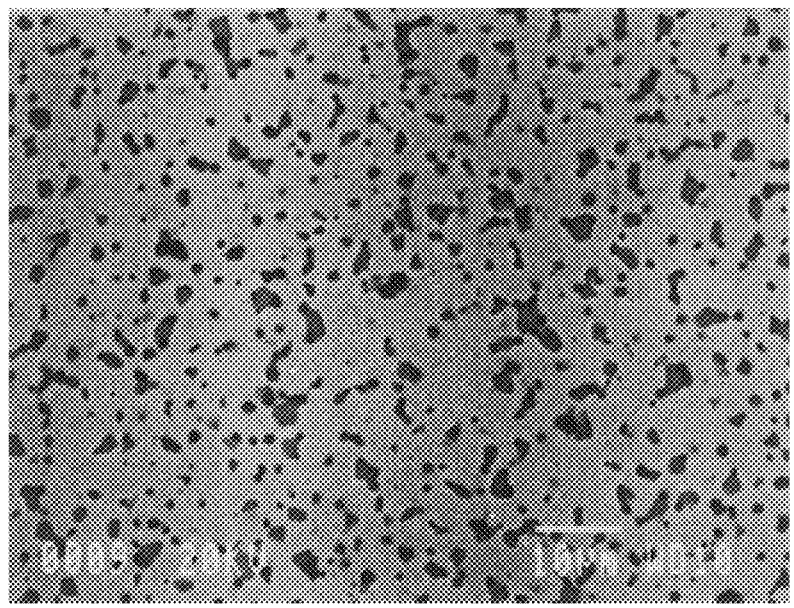
FIG. 1 is a scanning electron micrographs (1000X) of a sample according to the invention.
Figure 2:
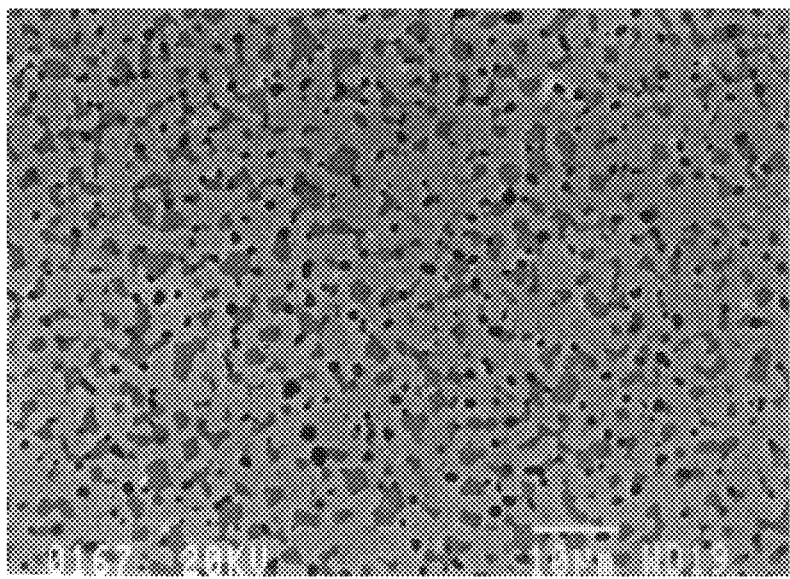
FIG. 2 is a scanning electron micrographs (1000X) of a second sample according to the invention.
Figure 3:
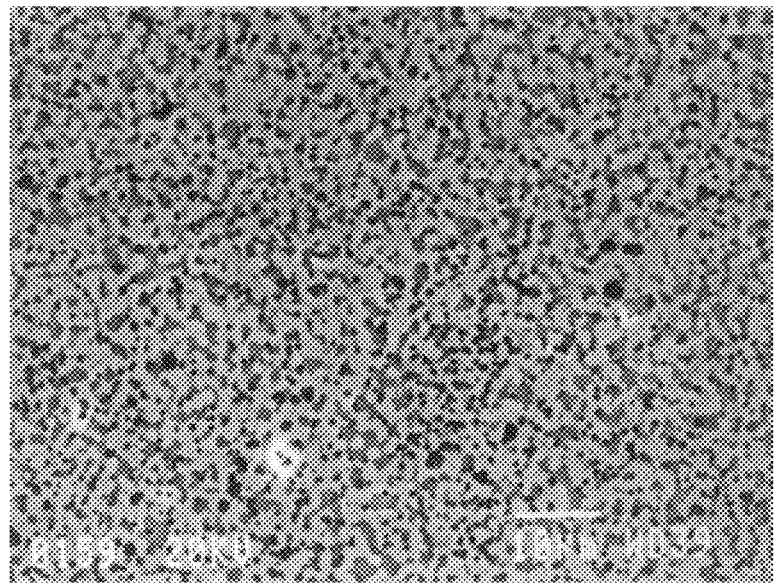
FIG. 3 is a scanning electron micrographs (1000X) of another sample according to the invention.

The present invention provides an $LaGaO_3$ sintered body comprising lanthanum, gallium, oxygen, and at least one of other elements and having three or more crystal phases of different composition formulae.

The molar quantities of lanthanum, gallium, and other elements other than oxygen (in total) will hereinafter be represented by $M_{La}$, $M_{Ga}$, and $M_o$.

The language "crystal phases of different composition formulae" as used herein is intended to mean crystal phases which may be either the same or different in kinds of constituent elements but are different in content of a certain element when expressed in terms of molar ratio. In detail, when one crystal phase contains lanthanum, gallium and other three elements at a molar ratio of a:b:c:d:e, the molar ratio of the same elements in another crystal phase is, for example, a':b:c:d:0, a':b':0:d:e, a:b':c':d':e, a':b':c':d':e', etc. provided that a≠a', b≠b', c≠c', d≠d', and e≠e'.

It is preferred for the $LaGaO_3$ sintered body to have at least a crystal phase nearer to the stoichiometric ratio (i.e., La:Ga:O=1:1:3) (hereinafter referred to as a first crystal phase) and another crystal phase whose composition formula is deviated from the stoichiometric ratio more than the first crystal phase (hereinafter referred to as a second crystal phase). The $LaGaO_3$ sintered body additionally has still another crystal phase different in composition formula from either the first or the second crystal phase (hereinafter referred to as a third crystal phase), which is usually a grain boundary phase.

The $LaGaO_3$ sintered body having the above-described structure can be formed by incorporation of aluminum. The content of aluminum in the sintered body, being expressed by the ratio of the molar quantity of aluminum (hereinafter "$M_{Al}$") to the total of $M_{La}$, $M_{Ga}$, and $M_o$ ($M_{Al}/(M_{La}+M_{Ga}+M_o)$), preferably ranges from 0.05 to 0 5, still preferably 0.05 to 0.2, particularly preferably 0.05 to 0.1. With the above ratio being less than 0.05, it is difficult to form three crystal phases having different composition formulae, and the sintered body will have insufficient mechanical strength although it exhibits sufficiently high conductivity. If the aluminum ratio exceeds 0.5, sufficient strength is obtained, but aluminum remains non-solid-dissolved and tends to react with other elements to form a different phase, which may reduce the conductivity.

The aluminum content in each of the first and second crystal phases, being expressed as $M_{Al}/(M_{La}+M_{Ga}+M_o)$, is preferably from 0.06 to 0.55 and from 0.04 to 0.6, respectively. The $LaGaO_3$ sintered body having at least these two crystal phases is assured of sufficient mechanical strength.

The ratio of the first or second crystal phase to the total crystal phases constituting the $LaGaO_3$ sintered body can be determined as follows. The cross section of an $LaGaO_3$ sintered body is polished for mirror finish and photographed under an electron microscope. An arbitrary straight line is drawn on the micrograph from one end to the other. Each of the total lengths of the first crystal phases and the second crystal phases appearing on the straight line is represented as a ratio, which will be referred to as a crystal phase ratio.

The crystal phase ratio of the first crystal phase to the total crystal phases is preferably 0.55 to 0.9, still preferably 0.6 to 0.9, particularly preferably 0.8 to 0.9, and that of the second crystal phase is preferably 0.4 or less, still preferably 0.25 or less, particularly preferably 0.18 or less.

An approximate volumetric ratio of the first or second crystal phase can be obtained as follows. At least two fields under an electron microscope are photographed, and two or more arbitrary straight lines are drawn on each micrograph. Lengths of the first crystal phases or the second crystal phases on each line are added up to obtain the length ratio to the total length of the line. The average of the resulting length ratios for each crystal phase is regarded as an approximate volumetric ratio of the crystal phase in the sintered body.

An $LaGaO_3$ sintered body is a perovskite-type oxide represented by general formula: $ABO_3$ and has an orthorhombic crystal structure of monoclinic phase. In this type of crystal structure, a dodecadentate ion having a large ionic radius is located at A site (centroid), and sexidentate ions having a smaller ionic radius are located at B sites to surround the central ion. In this theoretical $LaGaO_3$ sintered body, the ratio of the molar amount of the element at A site ($M_A$) to that of the element at B site ($M_B$), $M_A/M_B$, is 1, and lanthanum exists at A site while gallium at B site.

Where an $LaGaO_3$ sintered body contains elements other than lanthanum and gallium, for example, strontium, magnesium and aluminum, lanthanum and strontium exist at A site while gallium, magnesium and aluminum at B site. In this case, the $M_A/M_B$ deviates from the theoretical value. A preferred $M_A/M_B$ of the first crystal phase is 0.65 to 0.80, and that of the second crystal phase is 0.55 to 0.70.

The $LaGaO_3$ sintered body according to the invention which has three or more crystal phases having different composition formulae, particularly the one having the above-mentioned first and the second crystal phases can exhibit sufficient strength, having a four-point bending strength of 250 MPa or more, particularly 300 MPa or more, most preferably 350 MPa or more, as measured in accordance with JIS R1601. Further improvement on strength could be expected by properly controlling sintering conditions and the like. The compositions of crystal phases are subject to variation depending on the aluminum content thereby having controlled mechanical strength and controlled electrical conductivity.

An $LaGaO_3$ sintered body is generally made up of two phases, a crystal and a grain boundary phase. With this phase form, satisfactory electrical conductivity is maintained. In this invention, on the other hand, an element that is relatively difficult to solid-dissolve is added separately from a sintering aid, whereby a third phase, a fourth phase, etc. are formed in addition to the crystal phase and the grain boundary phase generally possessed by an $LaGaO_3$ sintered body to bring about improvement in strength. While the mechanism of action of the three or more phases different in composition formula that would account for the improvement in strength has not been elucidated as yet, it will be recognized from Examples hereinafter given that addition of, e.g., alumina definitely causes a new crystal phase of different composition formula to emerge and that improvement on the strength of an $LaGaO_3$ sintered body can result.

The invention provides a sensor device comprising an oxide ion-conducting solid electrolyte and a pair of electrodes formed on the solid electrolyte, in which the electrodes contains at least one of a mixed oxide and a metal oxide. The sensor device of the invention has high oxygen pumping ability.

Any materials known as an oxide ion-conducting solid electrolyte for a sensor device can be used in the invention. Those which can be used below 1000° C. are preferred. To widen the choice of noble metals as an electrode material, oxide ion-conducting solid electrolytes which can be used at 800° C. or lower are still preferred. Those which can be used practically at 700° C. or lower, such as an $LaGaO_3$ mixed oxide ($LaGaO_3$ oxide), a $ZrO_2$ oxide or a $CeO_2$ oxide, are especially preferred. In particular, an $LaGaO_3$ oxide is preferred from the standpoint of performance, and a $ZrO_2$ oxide is suited from the viewpoint of stability and mechanical strength.

As a material for the oxide ion-conducting solid electrolyte, the above mentioned $LaGaO_3$ sintered body comprising lanthanum, gallium, oxygen and at least one of other elements and having three or more crystal phases of different composition formulae is preferably used from the viewpoint of mechanical strength. In this case, the electrode for the sensor may or may not contain at least one of a mixed oxide and a metal oxide.

The $LaGaO_3$ mixed oxide includes $La_{0.9}Sr_{0.1}Ga_{0.8}Mg_{0.2}O_3$ (hereinafter referred to as LSGM), which is characterized by its high oxide ion conductivity compared with conventional yttrium-stabilized zirconia (YSZ). Use of LSGM as a solid electrolyte makes it possible to significantly lower the working temperature of the sensor device.

The $ZrO_2$ oxide includes $Y_2O_3$—$ZrO_2$ (i.e., YSZ) and $Sc_2O_3$—$ZrO_2$. YSZ is a typical oxide ion conductor and is preferred for its stability and mechanical strength. $Sc_2O_3$—$ZrO_2$ has a higher oxide ion conductivity than YSZ and is preferred where weight is put on performance.

The $CeO_2$ oxide includes $Gd_2O_3$—$CeO_2$, $Sm_2O_3$—$CeO_2$, and $Y_2O_3$—$CeO_2$. These $CeO_2$ oxides also have a higher oxide ion conductivity than YSZ and is therefore capable of reducing the working temperature of the sensor device.

The electrodes formed on the oxide ion-conducting solid electrolyte may contain at least one of a mixed oxide and a metal oxide. The oxygen pumping ability of the oxide ion-conducting solid electrolyte can be increased by this structure, and the working temperature of the sensor device can be lowered thereby.

The metal oxide to be incorporated into the electrode is selected from those capable of increasing the output current density from the sensor device, i.e., oxygen pumping ability, such as inorganic metal oxides, e.g., $MnO_2$, $MoO_3$, $Nd_2O_3$, $Fe_2O_3$, $WO_3$, $Nb_2O_5$, $Ta_2O_5$, $TiO_2$, $In_2O_3$, $IrO_2$, $Rh_2O_3$, CuO, and $CuO_2$. A metallo-organic or organometallic compound of a metal species, such as an organic acid salt and a resinate, can be used as a precursor of the inorganic metal oxide, which is added to a conductor paste and converted to the corresponding metal oxide on firing. Of the above-enumerated metal oxides, $MnO_2$ is particularly preferred for obtaining excellent oxygen pumping ability.

Similarly to the above-mentioned metal oxide, the mixed oxide to be incorporated into the electrode is selected from those capable of increasing the output current density from the sensor device, which is in proportion to oxygen pumping ability, such as $LaGaO_3$ oxide ($LaGaO_3$-based mixed oxide), $LaMnO_3$ oxide ($LaMnO_3$-based mixed oxide) and $LaCrO_3$ oxide ($LaCrO_3$-based mixed oxide). $LaGaO_3$ oxide, especially LSGM, is preferred from the viewpoint of oxygen pumping ability.

Addition of the metal oxide, such as $MnO_2$, and/or the mixed oxide, such as $LaGaO_3$ oxide, to the noble metal electrode results in great reduction in interfacial resistance between the electrode and the oxide ion-conducting solid electrolyte, which leads to high oxygen pumping ability. The total amount of the metal oxide and the mixed oxide to be added is preferably 0.1 to 50% by weight, still preferably 10 to 40% by weight, particularly preferably 10 to 35% by weight, based on the noble metal. It is preferred that both of the metal oxide, such as $MnO_2$, and the mixed oxide, such as $LaGaO_3$ oxide, be added. For example, a pair of Pt or Au electrodes containing 20% by weight of $MnO_2$ and 14% by weight of LSGM (34% by weight in total) based on Pt or Au secure extremely excellent oxygen pumping ability.

According to the invention, the oxygen pumping ability of a sensor device using a pair of Pt electrodes at 700° C. can be increased 18 or more times by addition of an $LaGaO_3$ mixed oxide or twice or more times by addition of a $ZrO_2$ oxide. Where Au electrodes are used, the oxygen pumping ability at 700° C. can be increased 100 or more times by addition of an $LaGaO_3$ mixed oxide or 6 or more times by addition of a $ZrO_2$ oxide. As a result, the sensor device of the invention can operate at far lower temperatures than conventional ones.

The electrodes which can be used in the invention comprise at least one element selected from the group consisting of Pt, Au, Pd, Ir, Rh, In, Ag, Tl, and Cu. Where it is desired to form the electrodes and the oxide ion-conducting solid electrolyte by simultaneous firing, it is preferred to use Pt having a high melting point as a main electrode material. If desired, metals that will lessen the catalysis of Pt, such as Au, Ir, Rh, In, Cu, Ag, and Tl, can be added to the Pt-based electrodes.

While conventional Au electrodes have failed to output signals at low working temperature, the Au electrodes according to the invention generate a sufficient output current density. Where the electrodes are formed by baking according to a thick film technology, the above-described various electrode materials can be used in an arbitrary combination. In this case, too, it is preferred for the characteristics to use Pt or Au as a main electrode material.

If an LaGaO$_3$ powder to be sintered has a large particle size, it is difficult to obtain a dense sintered body. That is, a green body of the powder or a sintered body obtained therefrom develops cracks, and observation of the sintered body under a scanning electron microscope (SEM) reveals gathering of pores.

The present inventors have found that a dense LaGaO$_3$ sintered body having a sinter density of 94% based on the theoretical density can be obtained by using a raw LaGaO$_3$ powder having its average particle size controlled to 1.7 μm or smaller (excluding 0 μm), by, for example, wet grinding. The present invention has been completed based on this finding.

The invention provides an LaGaO$_3$ sintered body whose surface roughness profile (roughness curve) determined according to JIS B0601 shows that the proportion of valleys (i.e., surface concave portion) below the mean line having a size less than 10 μm (excluding 0 μm, more specifically a size of less than 10 μm and not less than 4 μm) in all the valleys (all the concave portions) below the mean line is 50% or more in number, the size being the distance between two adjacent intersections of the mean line with the roughness profile forming one or more valleys (concave portions) below the mean line. This LaGaO$_3$ sintered body may be the above-mentioned LaGaO$_3$ sintered body comprising lanthanum, gallium, oxygen, and at least one of other elements and having three or more crystal phases of different composition formulae.

Since the number of valleys (concave portions) whose size is less than 10 μm is 50% or more of all the valleys below the mean line, the LaGaO$_3$ sintered body of the invention is very dense. Therefore, it has few such defects as cracks and exhibits excellent performance properties, such as high strength, durability, and oxide ion conductivity, and is the most suitable as, for example, a sensor device.

The term "surface" as used for the LaGaO$_3$ sintered body means the surface under analysis for obtaining a roughness profile or for measuring the size of valleys. Therefore, the surface includes not only the outer surface of the LaGaO$_3$ sintered body of the invention but a cut surface of the LaGaO$_3$ sintered body.

The term "roughness profile (roughness curve)" as determined according to JIS B0601 denotes a curve obtained by cutting off from an unfilter profile (sectional profile or sectional curve) the waviness component longer than a prescribed wavelength. The "unfilter profile (sectional profile)" is the surface profile which appears on cutting a surface to be assessed with a plane perpendicular to the surface.

The term "mean line" indicates a straight line or curve having a geometric form of the surface measured within a sampling length which is decided so that the sum of the squares of the deviations of the roughness profile from the "mean line" may be the least (i.e., the line determined by a method of least squares).

The term "valley (concave portion) below the mean line of the roughness profile" is intended to means a depression where the "unfilter profile (sectional profile)" as a straight line of "the vally (concave portion) of the unfilter profile" is converted to the roughness profile (as a segment) and is defined to be a depression below the mean line which appears on the roughness profile as a valley (concave portion) formed by the curve connecting adjacent two points crossing the mean line.

In the present invention, the valleys or depressions (concave portions) below the mean line are referred to surface valleys (surface concave portions). The surface valleys are considered to be attributed to exposure of pores present in a sintered body.

It is preferred that the LaGaO$_3$ sintered body of the invention has a sinter density of 94% or more of the theoretical density. Because the sintered body of the invention has small surface valleys (meaning small pores), it can have a sinter density of 94% or higher in terms of a relative density or density ratio to the theoretical density.

It is preferred that 87% or more of the surface valleys have a size less than 10 μm. In this preferred embodiment, the sintered body has extremely small and uniformly dispersed surface valleys (that is, the pores are extremely small and uniformly dispersed) and are therefore particularly superior in strength and durability.

It is also preferred for the sintered body to have a sinter density of 97% or more of the theoretical density. Because the sintered body of this embodiment has smaller surface valleys (meaning smaller pores), it can have a relative density of 97% or higher.

It is preferred that the LaGaO$_3$ sintered body be prepared from an LaGaO$_3$ powder having an average particle size of 1.7 μm or smaller. The powder as a raw material is particles to be used for forming a green body. That is, the powder is either directly or as mixed with a solution formed into a green body.

Starting with powder having an average particle size of 1.7 μm or smaller, there is obtained a dense LaGaO$_3$ sintered body whose surface roughness profile shows that the proportion of surface valleys having a size less than 10 μm in all the surface valleys is 50% or more in number. Where starting with LaGaO$_3$ powder having a smaller average particle size, e g., 1.4 μm or smaller, there is obtained a denser sintered body in which the proportion of surface valleys having a size less than 10 μm in all the surface valleys is 87% or more in number. In other words, a still preferred range of the average particle size of the starting powder is 1.4 μm or smaller.

The invention provides an LaGaO$_3$ sintered body prepared from an LaGaO$_3$ powder having an average particle size of 1.7 μm or smaller (particularly 1.4 μm or smaller) which has a relative density of 94% or more (particularly 97% or more). In this embodiment, a dense LaGaO$_3$ sintered body having a relative density of 94% or more (particularly 97% or more) can be obtained by using LaGaO$_3$ particles having an average particle size of 1.7 μm or smaller (particularly 1.4 μm or smaller).

The invention further provides a process for producing the above-described LaGaO$_3$ sintered body which comprises using an LaGaO$_3$ powder having an average particle size of 1.7 μm or smaller (excluding 0 μm) as a raw material.

By use of LaGaO$_3$ particles having an average particle size of 1.7 μm or smaller as a raw material to be formed into a green body, there is obtained a dense LaGaO$_3$ sintered body having a relative density of 94% or more and surface valleys having a size less than 10 μm in the proportion of 50% or more in number to the total surface valleys. Where LaGaO$_3$ particles having a smaller average particle size (e.g., 1.4 μm or smaller) are used as a raw material, there is obtained a denser LaGaO$_3$ sintered body having a relative density of 97% or more and surface valleys having a size less than 10 μm in the proportion of 87% or more.

The LaGaO$_3$ sintered body can be produced through the following procedures (1) to (3).

(1) The LaGaO$_3$ powder as a raw material can be prepared by conventional methods, such as a coprecipitation method, a sol-gel method, and spray pyrolysis.

The coprecipitation method comprises uniformly mixing powdered starting materials in an aqueous solution and chemically precipitating the mixed components as a solid phase by making use of a change in solubility.

The sol-gel method comprises preparing sol by mixing aqueous solutions of necessary components (part of the components may be mixed in the form of fine powder), dehydrating the sol to make it gel while maintaining the mixed state, and calcining the gel into an oxide powder.

The spray pyrolysis comprises mixing finely powdered starting materials with water, a binder and other additives to prepare a slurry and spraying the slurry into a drying furnace, into which hot air is being blown, by means of an atomizer, such as a spray nozzle or a spinning disk. The sprayed and scattered droplets are dried and solidified instantaneously while taking a spherical shape, the form of the free surface of droplets.

(2) The LaGaO$_3$ powder as a raw material can be wet ground to have a controlled average particle size. Specifically, the LaGaO$_3$ particles are put in a resin-made pot and wet ground together with iron-cored resin balls or ceramic balls of silicon nitride, zirconia, alumina, etc. Even if the resin separated from the pot or the resin balls is incorporated into the grinds, it will be burned out while fired and give no adverse effects to the sinter composition.

(3) The raw material having been wet ground is made into a green body, which is fired to obtain the LaGaO$_3$ sintered body.

The above-mentioned wet grinding in a solvent is an advantageous means for supplying a stable LaGaO$_3$ material because a hydrous lanthanum compound contained in the starting material does not undergo denaturation. Solvents which can be used in the wet grinding include not only organic ones, such as ethanol and acetone, but water.

The LaGaO$_3$ powder as a raw material preferably includes LaGaO$_3$-based mixed oxide particles. The LaGaO$_3$-based mixed oxide particles are one or more kinds of LaGaO$_3$ with part of its La or Ga displaced with Sr, Mg, etc. by substitutional solid dissolution, i.e., La$_{1-x}$Sr$_x$Ga$_{1-y}$Mg$_y$O$_3$, La$_{1-x-y}$Ln$_x$Sr$_y$Ga$_{1-z}$Mg$_z$O$_3$, and La$_{1-x}$Sr$_x$Ga$_{0.8}$Mg$_{0.2-y}$Co$_y$O$_3$. When the LaGaO$_3$ sintered body is the above-mentioned LaGaO$_3$ sintered body comprising lanthanum, gallium, oxygen, and at least one of other elements and having three or more crystal phases of different composition formulae, the LaGaO$_3$ sintered body may be produced by mixing the LaGaO$_3$ powder with Al as a raw material.

The sensor device to which the LaGaO$_3$ sintered body of the invention is applicable includes an oxygen sensor, a hydrocarbon sensor, and a NO$_x$ sensor.

The invention will now be illustrated in greater detail with reference to Examples. It should be understood that the invention is not construed as being limited thereto.

EXAMPLE 1

1) Preparation of Test Pieces 1A to 8A
i) Preparation of Mixed Powder

Nitrates each of lanthanum, gallium, strontium, and magnesium were weighed at a La:Ga:Sr:Mg molar ratio of about 0.9:0.1:0.8:0.2 and dissolved in a requisite amount of pure water. The pH of the solution was adjusted to form a coprecipitate of the elements, which was collected by filtration, dried, and calcined to obtain a mixed powder of the oxides of the elements. The mixed powder was put in a resin pot, and a weighed quantity of alumina powder was added thereto to give an aluminum content of about 0.05, 0.08, 0.1, 0.2, 0.3, 0.33, 0.4 or 0.5 mol % based on the total molar quantity of lanthanum, gallium, strontium, and magnesium in the mixed powder. The mixture in the pot was wet mixed for 16 hours. The resulting slurry was transferred to a stainless steel bowl, dried on a hot water bath with a submerged heater, and passed through a 60 mesh sieve to obtain a mixed powder of lanthanum oxide, gallium oxide, strontium oxide, magnesium oxide, and aluminum oxide.

ii) Forming and Firing

The mixed powder was formed in a mold into a 70 mm long, 70 mm wide and 10 mm thick body. The body was vacuum packaged in a polyurethane bag and pressed by hydrostatic pressing (CIP) under 1.5 ton/cm$^2$ for 10 seconds. The resulting green body was sintered by firing in the air at 1500° C. for 3 hours. The sintered body was cut and flat polished to prepare test pieces in conformity to JIS, which were numbered individually from 1A to 8A in an ascending order of the aluminum content.

2) Preparation of Comparative Test Pieces 1A and 2A

A mixed oxide powder was prepared by coprecipitation in the same manner as in (1-i) above, except that alumina was not added. The mixed powder was formed and fired in the same manner as in (1-ii) to prepare a comparative test piece 1A.

Zirconia and yttria were weighed at a Zr:Y molar ratio of 0.955:0.045, ground, and wet mixed to obtain a mixed powder. The mixed powder was formed and fired in the air at 1500° C. for 2 hours. The sintered body was processed in the same manner as in (i–ii) to prepare a comparative test piece 2A comprising YSZ.

3) Analysis on Test Pieces
i) Quantitative Analysis

The elements making up test pieces 1A to 8A and comparative test piece 1A were analyzed with an electron probe X-ray microanalyzer (JXA-8800M, supplied by JEOL Ltd.). The results obtained are shown in Table 1 immediately below.

TABLE 1

| | | Molor Ratio | | |
|---|---|---|---|---|
| Sample | Element | Light Hue Phase | Intermediate Hue Phase | Deep Hue Phase |
| Comparative Test Piece 1A | La | 53.24 | 0 | 0.21 |
| | Sr | 5.34 | 0 | 0.02 |
| | Ga | 37.71 | 0 | 0.06 |
| | Mg | 3.71 | 0 | 99.71 |
| | Al | 0.01 | 0 | 0 |
| Test Piece 1A | La | 38.84 | 17.42 | 0.82 |
| | Sr | 4.36 | 20.83 | 0.13 |
| | Ga | 43.49 | 54.44 | 0.59 |
| | Mg | 6.60 | 2.80 | 97.56 |
| | Al | 6.72 | 4.51 | 0.89 |
| Test Piece 2A | La | 40.33 | 17.72 | 1.76 |
| | Sr | 2.58 | 20.58 | 1.51 |
| | Ga | 42.18 | 52.71 | 2.87 |
| | Mg | 4.11 | 2.09 | 92.95 |
| | Al | 10.79 | 6.89 | 0.91 |
| Test Piece 3A | La | 40.47 | 17.84 | 0.35 |
| | Sr | 1.54 | 20.12 | 0.18 |
| | Ga | 40.88 | 51.08 | 5.82 |
| | Mg | 2.36 | 2.45 | 93.13 |
| | Al | 14.75 | 8.50 | 0.52 |

TABLE 1-continued

|  |  | Molor Ratio | | |
|---|---|---|---|---|
| Sample | Element | Light Hue Phase | Intermediate Hue Phase | Deep Hue Phase |
| Test Piece 4A | La | 39.24 | 16.68 | 0.89 |
|  | Sr | 1.70 | 20.31 | 0.87 |
|  | Ga | 29.24 | 45.10 | 44.70 |
|  | Mg | 2.01 | 2.30 | 34.95 |
|  | Al | 27.80 | 15.61 | 18.60 |
| Test Piece 5A | La | 37.53 | 15.88 | 0.14 |
|  | Sr | 2.27 | 21.23 | 0.01 |
|  | Ga | 21.04 | 39.73 | 39.15 |
|  | Mg | 0.14 | 0.05 | 35.63 |
|  | Al | 39.02 | 23.12 | 25.07 |
| Test Piece 6A | La | 39.21 | 14.88 | 0.49 |
|  | Sr | 1.31 | 20.97 | 0.17 |
|  | Ga | 13.74 | 32.94 | 31.21 |
|  | Mg | 0.15 | 0.91 | 34.33 |
|  | Al | 45.59 | 30.31 | 33.79 |
| Test Piece 7A | La | 38.82 | 15.43 | 0.14 |
|  | Sr | 1.12 | 21.79 | 0.02 |
|  | Ga | 17.40 | 37.75 | 36.25 |
|  | Mg | 0.45 | 0.03 | 35.46 |
|  | Al | 42.21 | 25.00 | 28.14 |
| Test Piece 8A | La | 38.18 | 15.51 | 0.52 |
|  | Sr | 1.42 | 2.27 | 0.13 |
|  | Ga | 10.16 | 19.86 | 24.32 |
|  | Mg | 0.19 | 3.58 | 33.21 |
|  | Al | 50.05 | 58.78 | 41.83 | ii) $M_A/M_B$

The ratio of the total molar quantity of La and Sr that were assumed to be located at A site to the total molar quantity of Ga, Mg, and Al that were assumed to be located at B site, $M_A/M_B$ was calculated from the results of Table 1. The results of calculation are shown in Table 2 below.

TABLE 2

|  | Light Hue Phase | | Intermediate Hue Phase | | Deep Hue Phase | |
|---|---|---|---|---|---|---|
| Sample | A Site (%) | B Site (%) | A Site (%) | B Site (%) | A Site (%) | B Site (%) |
| Comparative Test Piece 1A | 58.6 | 41.4 | 0 | | 0.2 | 99.8 |
| Test Piece 1A | 43.2 | 56.8 | 38.2 | 61.8 | 1.0 | 99.0 |
| Test Piece 2A | 42.9 | 57.1 | 38.3 | 61.7 | 3.3 | 96.7 |
| Test Piece 3A | 42.0 | 58.0 | 38.0 | 62.0 | 0.5 | 99.5 |
| Test Piece 4A | 40.9 | 59.1 | 37.0 | 63.0 | 1.8 | 98.2 |
| Test Piece 5A | 39.8 | 60.2 | 37.1 | 62.9 | 0.2 | 99.8 |
| Test Piece 6A | 40.5 | 59.5 | 35.8 | 64.2 | 0.6 | 99.4 |
| Test Piece 7A | 39.9 | 60.1 | 37.2 | 62.8 | 0.2 | 99.8 |
| Test Piece 8A | 36.6 | 60.4 | 17.8 | 82.2 | 0.6 | 99.4 | iii) Microscopic Observation

Figure 4:
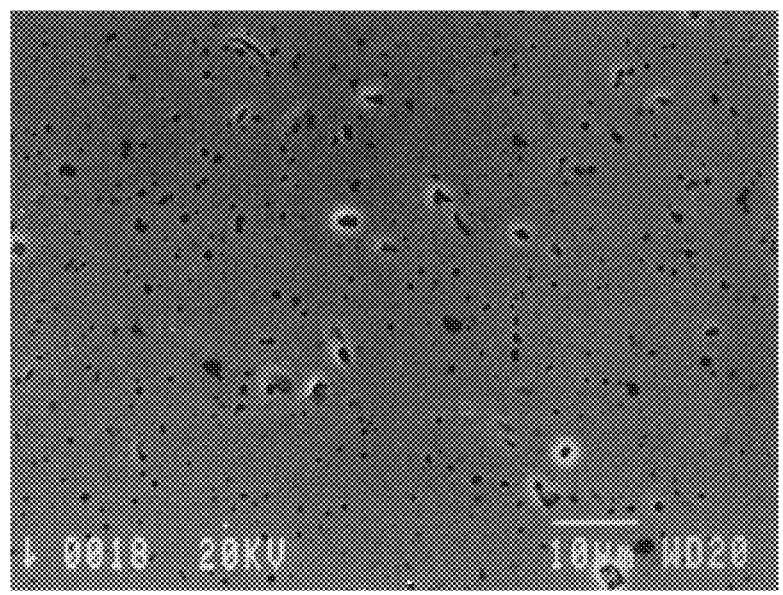
FIG. 4 is a scanning electron micrograph (1000X) of a comparative sample.

Each of test pieces 1A through 8A and comparative test piece 1A was mirror polished and photographed under a scanning electron microscope (JSM-840, manufactured by JEOL Ltd.) at a magnification of 1,000. The micrographs of test pieces 1A, 3A, 4A and comparative test piece 1A are shown in FIGS. 1 to 4, respectively. FIG. 4 displays two phases, a light hue phase and a deep hue phase, while FIGS. 1 to 3 additionally shows an intermediate hue phase. It is seen that the intermediate hue phase increases with an aluminum content.

iv) Crystal Phase Ratio

Three straight lines were drawn on each micrograph obtained in (iii) from one end to the other. The length of every crystal phase appearing on each line was measured to obtain the ratio of crystal phases of a kind per line. Then, an average of the crystal phase ratio of the three measurements was calculated. The results are shown in Table 3.

TABLE 3

| Sample | Number of Measurements and Average | Light Hue Phase (%) | Intermediate Hue Phase (%) | Deep Hue Phase (%) |
|---|---|---|---|---|
| Comparative Test Piece 1A | 1 | 99.1 | 0.0 | 0.9 |
|  | 2 | 100.0 | 0.0 | 0.0 |
|  | 3 | 99.1 | 0.0 | 0.9 |
|  | Avg. | 99.4 | 0.0 | 0.6 |
| Test Piece 1A | 1 | 84.9 | 7.3 | 7.8 |
|  | 2 | 83.5 | 8.7 | 7.8 |
|  | 3 | 89.9 | 6.4 | 3.7 |
|  | Avg | 86.1 | 7.5 | 6.4 |
| Test Piece 2A | 1 | 78.0 | 17.4 | 4.6 |
|  | 2 | 68.5 | 28.3 | 3.2 |
|  | 3 | 89.0 | 5.5 | 5.5 |
|  | Avg. | 78.5 | 17.1 | 4.4 |
| Test Piece 3A | 1 | 76.7 | 22.4 | 0.9 |
|  | 2 | 82.2 | 15.8 | 2.0 |
|  | 3 | 81.7 | 17.4 | 0.9 |
|  | Avg. | 80.2 | 18.5 | 1.3 |
| Test Piece 4A | 1 | 71.2 | 25.0 | 3.8 |
|  | 2 | 70.4 | 19.6 | 10.0 |
|  | 3 | 56.2 | 30.8 | 13.0 |
|  | Avg. | 65.9 | 25.1 | 8.9 |
| Test Piece 5A | 1 | 57.0 | 32.0 | 11.0 |
|  | 2 | 57.0 | 31.8 | 11.2 |
|  | 3 | 51.1 | 29.7 | 19.2 |
|  | Avg. | 55.0 | 31.2 | 13.8 |
| Test Piece 6A | 1 | 56.1 | 31.1 | 12.8 |
|  | 2 | 50.4 | 44.7 | 4.9 |
|  | 3 | 56.6 | 38.6 | 4.8 |
|  | Avg. | 54.4 | 38.1 | 7.5 |
| Test Piece 7A | 1 | 70.5 | 24.1 | 5.4 |
|  | 2 | 54.4 | 39.3 | 6.3 |
|  | 3 | 61.7 | 26.8 | 11.5 |
|  | Avg. | 62.2 | 30.1 | 7.7 |
| Test Piece 8A | 1 | 63.0 | 35.1 | 1.9 |
|  | 2 | 54.8 | 43.0 | 2.2 |
|  | 3 | 58.1 | 36.2 | 5.7 |
|  | Avg. | 58.6 | 38.1 | 3.3 |

Figure 5:
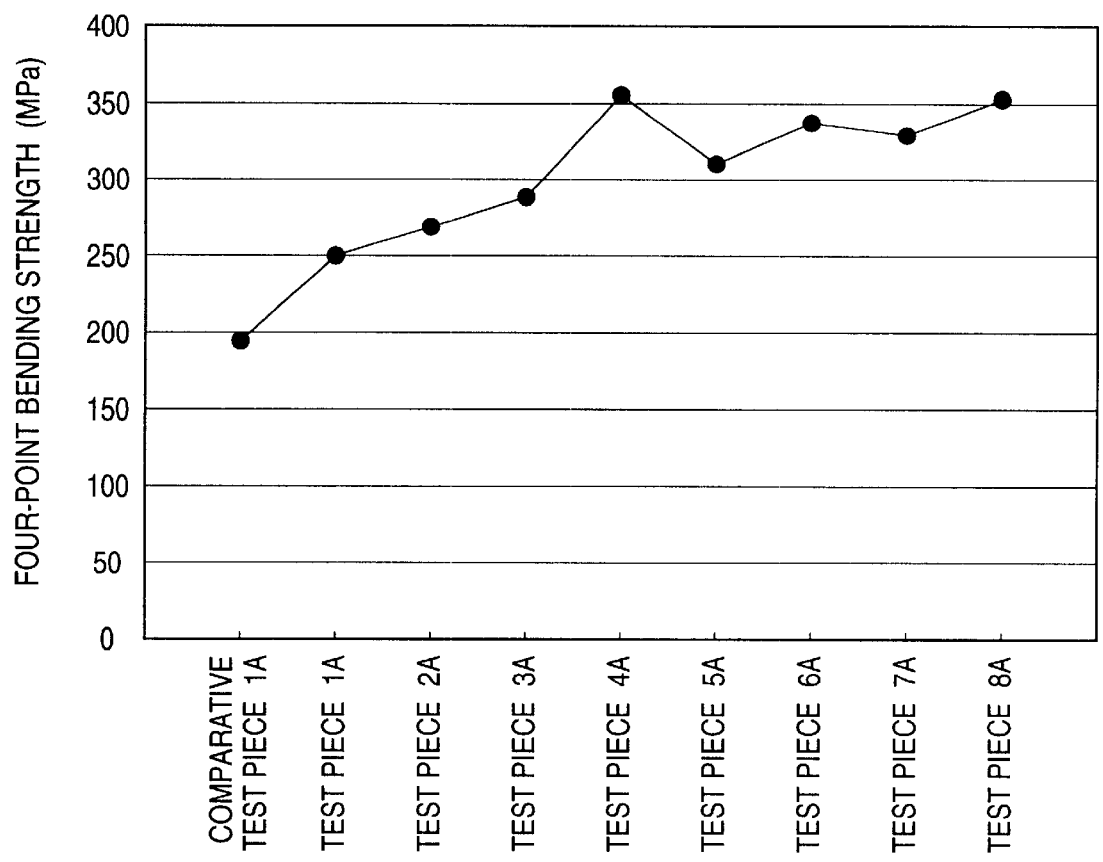
FIG. 5 is a graph showing the four-point bending strength of test pieces.

4) Evaluation of Mechanical Characteristics i) Density, Modulus of Elasticity, Poisson's Ratio, Fracture Toughness, Hardness, and Four-point Bending Strength The density, modulus of elasticity, Poisson's ratio, fracture toughness, hardness, and four-point bending strength of test pieces A1 to A8 and comparative test piece A1 were measured according to the following standards. The results are shown in Table 4 below. For better understanding, the results of the four-point bending test are graphically illustrated in FIG. 5. Standards of measurement:

Density: Archimedes' method

Modulus of elasticity: JIS R1602

Poisson's ratio: JIS R1607

Fracture toughness: JIS R1607

Hardness: JIS R1610

Four-point bending strength: JIS R1601

TABLE 4

| Sample | Density (g/cm³) | Modulus of Elasticity (GPa) | Poisson's Ratio | Fracture Toughness (MPa·m^0.5) | Hardness | Four-Point Bending Strength (MPa) |
|---|---|---|---|---|---|---|
| Comparative Test Piece 1A | 6.50 | 194 | 0.28 | 1.00 | 755 | 192 |
| Test Piece 1A | 6.51 | 199 | 0.29 | 1.69 | 810 | 250 |
| Test Piece 2A | 6.49 | 198 | 0.29 | 1.67 | 843 | 269 |
| Test Piece 3A | 6.41 | 205 | 0.28 | 2.12 | 846 | 287 |
| Test Piece 4A | 6.22 | 220 | 0.28 | 2.34 | 959 | 356 |
| Test Piece 5A | 5.99 | 229 | 0.28 | 2.12 | 968 | 309 |
| Test Piece 6A | 5.94 | 255 | 0.27 | 2.40 | 1078 | 336 |
| Test Piece 7A | 5.81 | 228 | 0.29 | 2.35 | 1010 | 328 |
| Test Piece 8A | 5.58 | 264 | 0.28 | 2.80 | 1088 | 354 | ii) Electrical Conductivity

Figure 6:
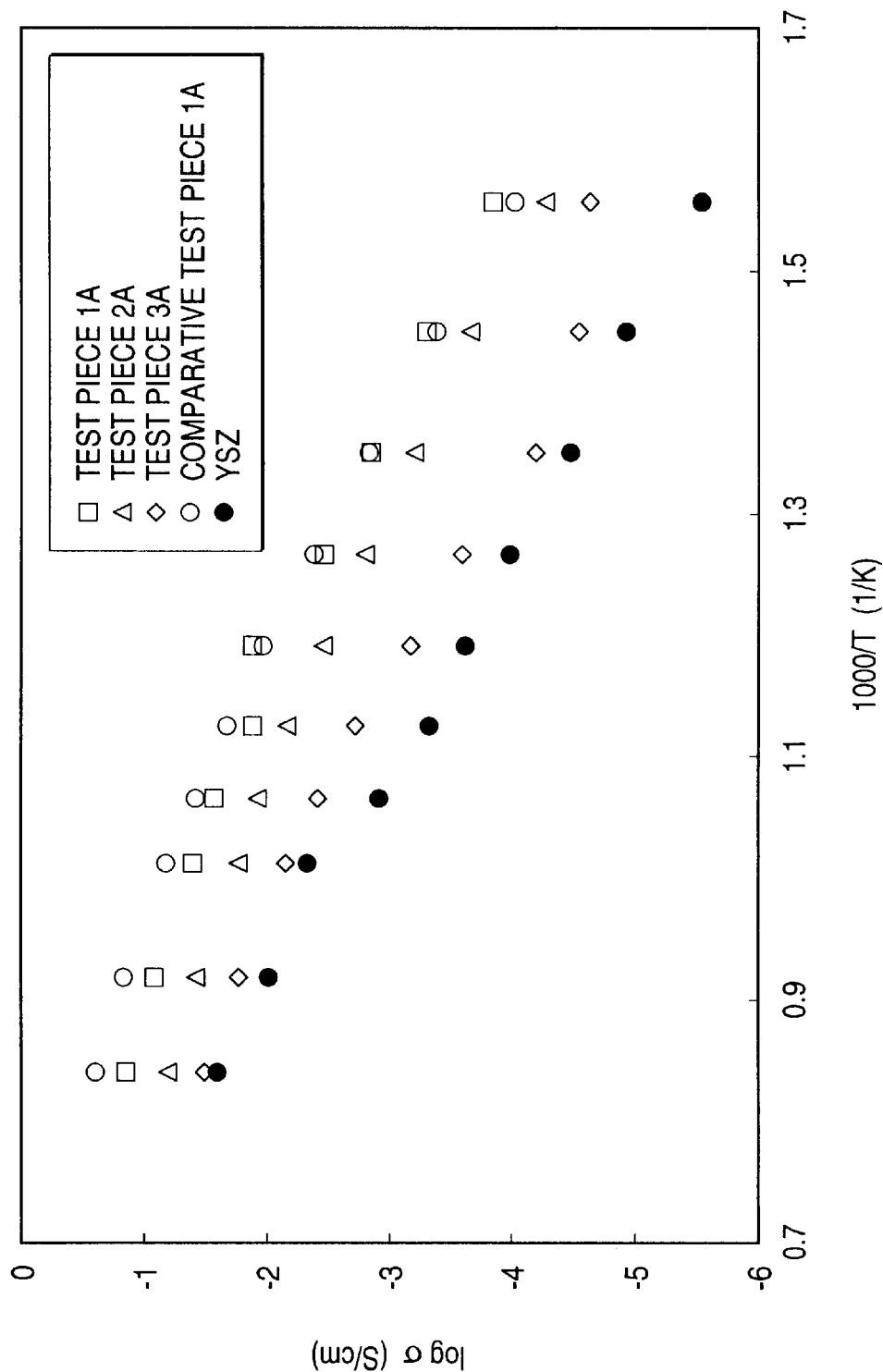
FIG. 6 is a graph showing the electrical conductivity of test pieces.

The electrical conductivity of test pieces 1A to 3A and comparative test pieces 1A was measured in the air at room temperature by a DC four probe method. The results are graphically shown in FIG. 6.

It is seen from FIGS. 1 to 4 that an intermediate hue phase develops by the addition of aluminum and that the area ratio of the intermediate hue phase increases with an increase of the aluminum content. Comparison of these results with Table 1 reveals that the intermediate hue phase is the second crystal phase shown in Table 1. According as the area ratio of the second crystal phase increases, the second crystal phase increases, and all the modulus of elasticity, fracture toughness and four-point bending strength also increase with the increase of the second crystal phase. It is also seen from FIG. 6 that test pieces 1A to 3A and comparative test piece 1A have higher conductivity than YSZ (comparative test piece 2A).

The practice of the invention is not limited to the above-described Example, and various changes and modifications can be made within the scope of the invention. For example, not being limited to the nitrates as used in Example, the raw material powders making up the mixed powder include carbonates, sulfates, hydroxides, chlorides, etc. of the elements, and mixtures thereof.

According to the invention, three or more crystal phases different in composition formula are formed in an $LaGaO_3$ sintered body by addition of a prescribed element or elements to bring about marked improvement on mechanical strength with an increase of a prescribed crystal phase without being accompanied by large reduction in conductivity. The invention thereby provides an $LaGaO_3$ sintered body that can be used in practical volume products and so forth.

EXAMPLE 2

(1) Preparation of Solid Electrolyte

LSGM powder prepared by a conventional coprecipitation method or YSZ powder containing 4.5 mol % of $Y_2O_3$ prepared by conventional spray drying was compressed by CIP into a 70 mm long, 70 mm wide and 10 mm thick green body. The green body was fired in the air at 1500° C. for 3 hours, cut to size, and flat polished to a thickness of 0.5 mm to obtain a solid electrolyte comprising LSGM or YSZ.

(2) Preparation of Electrode Paste

Pt powder or Au powder were mixed with $MnO_2$ and LSGM according to the formulation shown in Table 5 below and kneaded with prescribed amounts of ethyl cellulose (binder), Ionet S-20 manufactured by Sanyo Chemical Industries, Ltd. (dispersant) and butyl carbitol (viscosity modifier) in a mixing and grinding machine to prepare an electrode paste for electrodes C, D, E, or F.

(3) Preparation of Sensor Device

Figure 7:
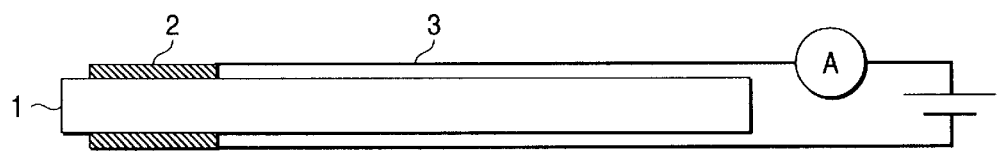
FIG. 7 schematically illustrates a sensor device prepared as a sample for evaluation.

Each electrode paste was applied to the solid electrolyte, and a Pt mesh having a Pt lead wire was attached thereon as a current collector. The applied paste was baked at 850° C. for 10 minutes to prepare a sensor device. For comparison, a sensor device was prepared in the same manner, except that a Pt or Au paste containing neither $MnO_2$ nor LSGM was applied and baked at 1500° C. or 850° C., respectively, for 10 minutes to form a Pt electrode (A in Table 5) or an Au electrode (B in Table 5). FIG. 7 schematically illustrates a sensor device.

TABLE 5

| Electrode | Electrode Composition (wt %) | | | |
|---|---|---|---|---|
| | Pt | Au | $MnO_2$ | LSGM |
| A* | 100 | 0 | 0 | 0 |
| B* | 0 | 100 | 0 | 0 |
| C | 80 | 0 | 20 | 0 |
| D | 0 | 80 | 20 | 0 |
| E | 66 | 0 | 20 | 14 |
| F | 0 | 66 | 20 | 14 |

*: comparative example (4) Evaluation of Sensor Device

The oxygen pumping ability of the sensor devices prepared in (3) above was evaluated as follows. The oxygen pumping ability can be evaluated from the current flowing with a voltage applied to the sensor device because both LSGM and YSZ are almost pure oxide ion-conducting solid electrolyte. The conditions of measurement were as follows.

Measuring temperature: 500° C., 600° C. or 700° C.

Gas composition: 20% $O_2$ and balance of $N_2$

Gas flow rate: 12 l/min

Applied voltage: 1 V

Figure 8:
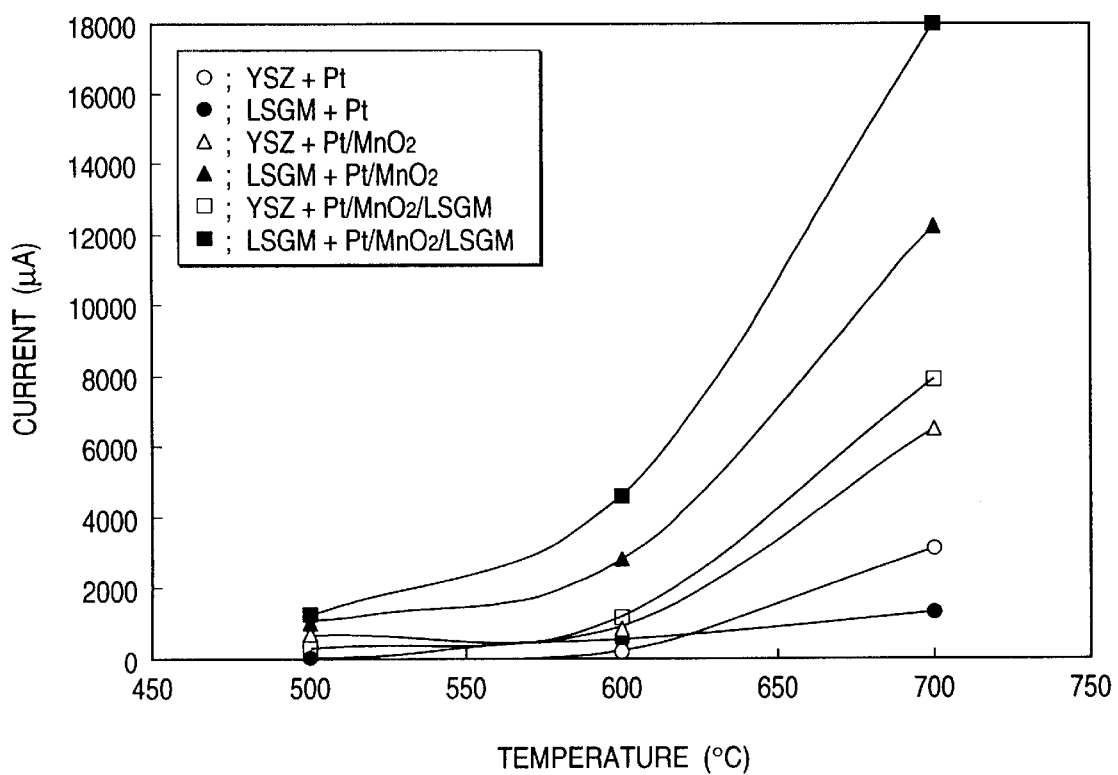
FIG. 8 is a graph showing temperature dependence of current of sensor devices using Pt-based electrodes.
Figure 9:
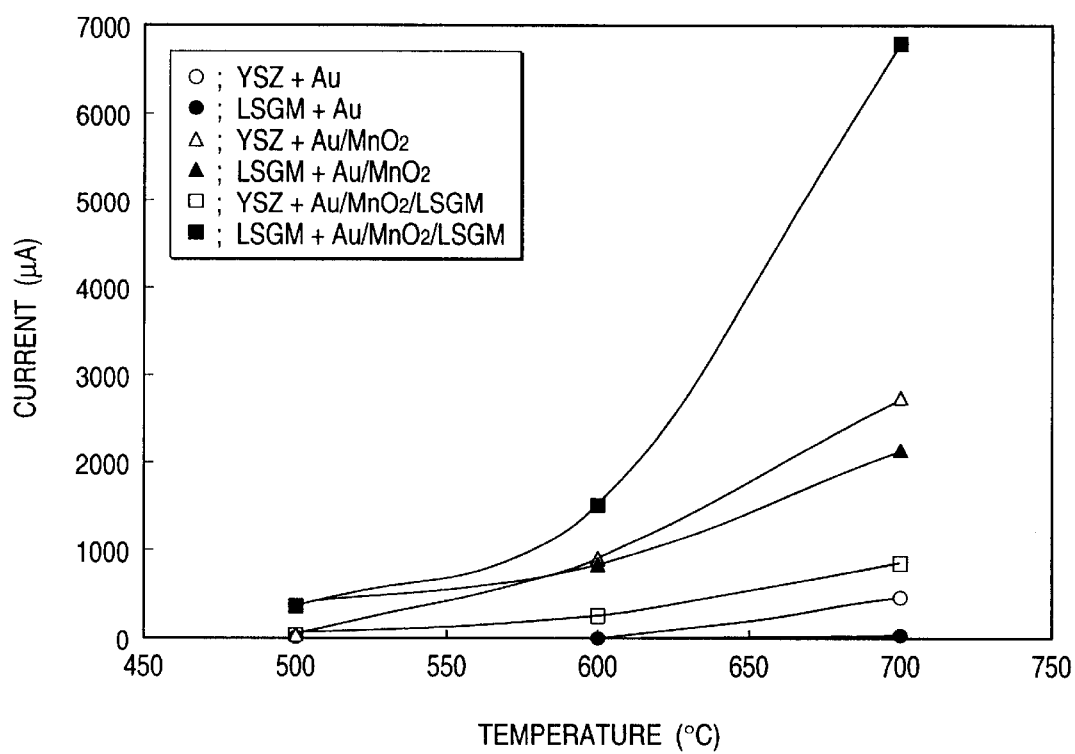
FIG. 9 is a graph showing temperature dependence of current of sensor devices using Au-based electrodes.

The results obtained from the sensor devices using a Pt-based electrode are shown in Table 6, and those from the sensor devices using an Au-based electrode are shown in Table 7. The temperature dependence of the current is shown in FIGS. 8 (Pt-based electrode) and 9 (Au-based electrode).

TABLE 6

| Sample No. | Electrode | Solid Electrolyte | Current (μA) | | |
|---|---|---|---|---|---|
| | | | 500° C. | 600° C. | 700° C. |
| 1B* | A | YSZ | 46.9 | 210.7 | 3131.1 |
| 2B | A | LSGM | 20.7 | 548.1 | 1272.9 |
| 3B | C | YSZ | 685.9 | 866.1 | 6532.9 |

TABLE 6-continued

| Sample No. | Solid Electrode | Electrolyte | Current ($\mu$A) 500° C. | 600° C. | 700° C. |
|---|---|---|---|---|---|
| 4B* | C | LSGM | 1001.8 | 2818.8 | 12311.7 |
| 5B | E | YSZ | 252.1 | 1147 | 7914 |
| 6B | E | LSGM | 1229.6 | 4637 | 17970 |

Note:
*Comparison

TABLE 7

| Sample No. | Solid Electrode | Electrolyte | Current ($\mu$A) 500° C. | 600° C. | 700° C. |
|---|---|---|---|---|---|
| 7B* | B | YSZ | —** | 20.38 | 474.7 |
| 8B | B | LSGM | —** | 11.19 | 54.59 |
| 9B | D | YSZ | 49 | 928.4 | 2754.3 |
| 10B* | D | LSGM | 403.8 | 835.6 | 2137.7 |
| 11B | F | YSZ | 50.7 | 257.8 | 873.8 |
| 12B | F | LSGM | 361.8 | 1516 | 6789 |

Note:
*Comparison
**Unmeasurable

It is seen that addition of $MnO_2$ or LSGM to a Pt electrode or Au electrode results in a great increase in current, indicating improved oxygen pumping ability. In particular, samples 5B and 6B having Pt-based electrodes and sample 12B having Au-based electrodes where both $MnO_2$ and LSGM were added exhibit remarkably improved oxygen pumping ability as is seen from the maximum current reached, which is 18 times that obtained from conventional sensor devices having Pt electrodes or 100 times that obtained from conventional sensor devices having Au electrodes. It is understood from these results that the sensor devices according to the present invention can work in lower temperatures.

According to the invention, the interfacial resistance between the oxide ion-conducting solid electrolyte and noble metal electrodes can be reduced greatly. As a result, the sensor device of the invention exhibits improved oxygen pumping ability and is capable of working in low temperatures below 700° C. Thus, the invention provides a means for accurately detecting easily combustible gas, such as hydrocarbons.

EXAMPLE 3
(a) Preparation of $LaGaO_3$ Sintered Body
(1) Preparation of Raw Material Nitrates of lanthanum, strontium, gallium or magnesium were weighed to give the stoichiometric composition of $La_{0.9}Sr_{0.1}Ga_{0.8}Mg_{0.2}O_3$ and dissolved in a predetermined amount of pure water. The pH of the solution was adjusted to form a coprecipitate, which was processed in a usual manner by filtration, drying, calcination, and grinding to prepare an $LaGaO_3$-based oxide powder.

(2) Particle Size Adjustment

The oxide powder was put in a resin pot together with a solvent and grinding balls selected appropriately as described below and wet ground for 1 hour. The resulting slurry was transferred to a stainless steel bowl, dried on a hot water bath with a submerged heater, and passed through a 60 mesh sieve to obtain an $LaGaO_3$-based oxide powder having the average particle size shown in Table 8 below. The particle size was measured with a laser diffraction type particle size distribution measuring apparatus (LA-500, manufactured by Horiba).

The particle size adjustment was achieved by selection of the grinding balls to be used in the wet grinding. That is, ceramic balls of alumina or silicon nitride were used for obtaining particles of small size, and resin balls were used for obtaining particles of relatively large size. The thus prepared oxide powders were designated sample Nos. 1C to 3C, as shown in Table 8.

For comparison, a $LaGaO_3$-based oxide powder having the average particle size shown in Table 8 was prepared without conducting wet grinding (designated sample No. 4C).

(3) Forming

Sixty grams of each sample was formed in a mold into a 70 mm long, 70 mm wide and 10 mm thick body. The body was vacuum packaged in a polyurethane bag and pressed by hydrostatic pressing (CIP) under 1.5 ton/cm² for 10 seconds.

(4) Firing

The resulting green body was sintered by firing in the air at 1500° C. for 3 hours to obtain an $LaGaO_3$ sintered body.

(b) Evaluation of $LaGaO_3$ Sintered Body
(1) Density

The sinter density of the resulting $LaGaO_3$ sintered body was measured by Archimedes' method, and a relative density was obtained as a ratio of the sinter density to the theoretical density of $La_{0.9}Sr_{0.1}Ga_{0.8}Mg_{0.2}O_3$ (=6.65 g/cm³). The results obtained are shown in Table 8.

TABLE 8

| Sample No. | Average Particle Size ($\mu$m) | Density (g/cm³) | Relative Density (%) |
|---|---|---|---|
| 1C | 1.65 | 6.29 | 94.5 |
| 2C | 1.27 | 6.48 | 97.4 |
| 3C | 1.36 | 6.55 | 98.5 |
| 4C (comparison) | 5.52 | 6.11 | 91.8 |

As is apparent from Table 8, a dense $LaGaO_3$ sintered body having a relative density of 94% or higher can be obtained by starting with an $LaGaO_3$-based oxide powder having an average particle size of not greater than 1.7 $\mu$m. In particular, a denser sintered body having a relative density of 97% or higher can be obtained by using an $LaGaO_3$-based oxide powder having an average particle size of 1.4 $\mu$m or smaller.

(2) Determination of Surface Profile

The surface valleys, being defined to be the pores of the sintered body exposed on the surface, were examined as follows. Each sample was buried in a resin, and its surface was polished for mirror finish. Polishing for mirror finish is machining by relative movement under pressure with an ultrafine wheel stone or loose abrasive particles to make a surface with reduced surface roughness and high dimensional accuracy.

The roughness of the polished surface was measured in accordance with JIS B0601 to prepare a roughness profile. The assessment was made with a stylus-type profilometer (SE-30D, manufactured by Kosaka Kenkyusho) specified in JIS B0651 under the following conditions.

Figure 10:
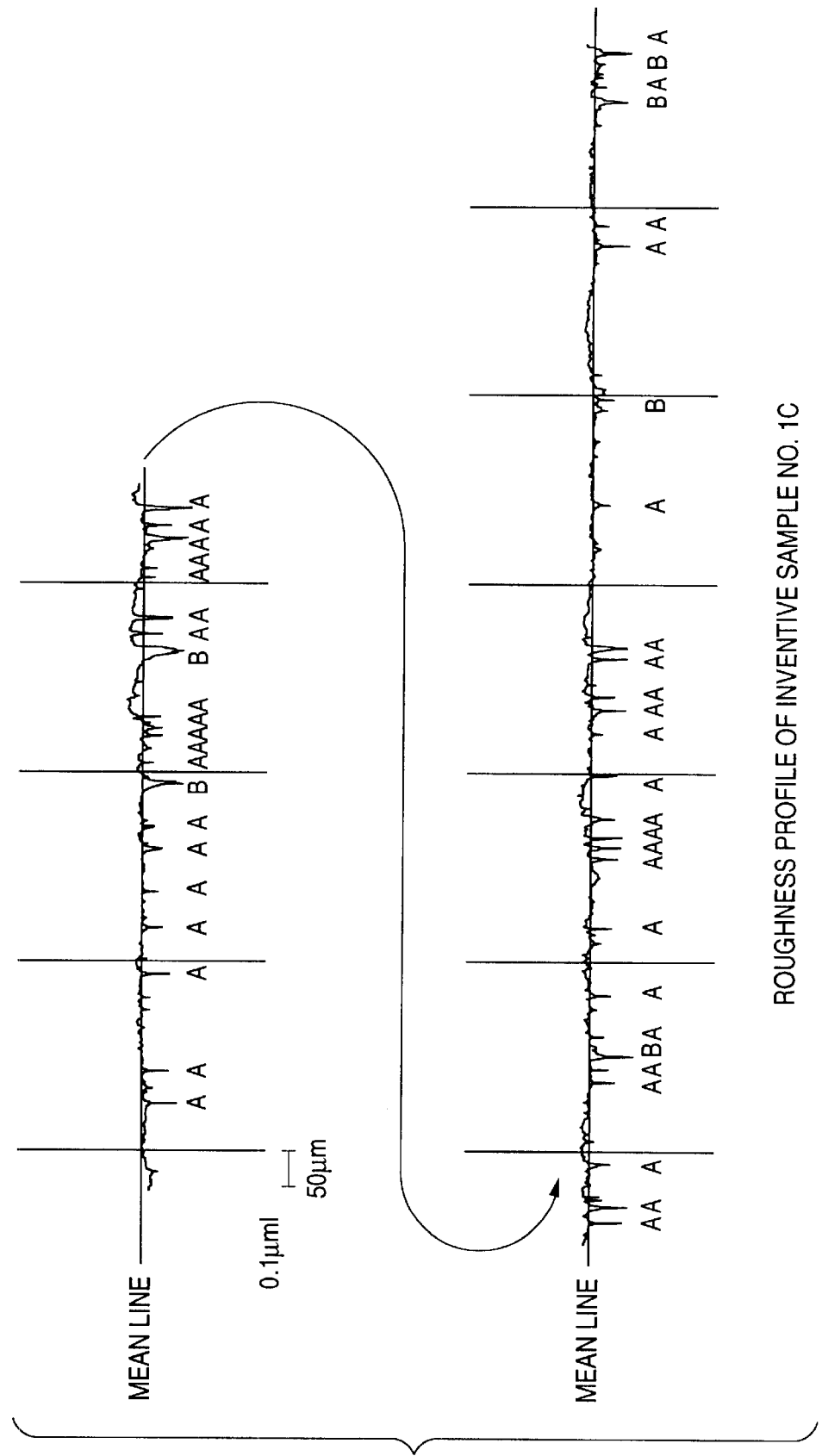
FIG. 10 is a surface roughness profile of Inventive Sample No. 1C according to the present invention.
Figure 11:
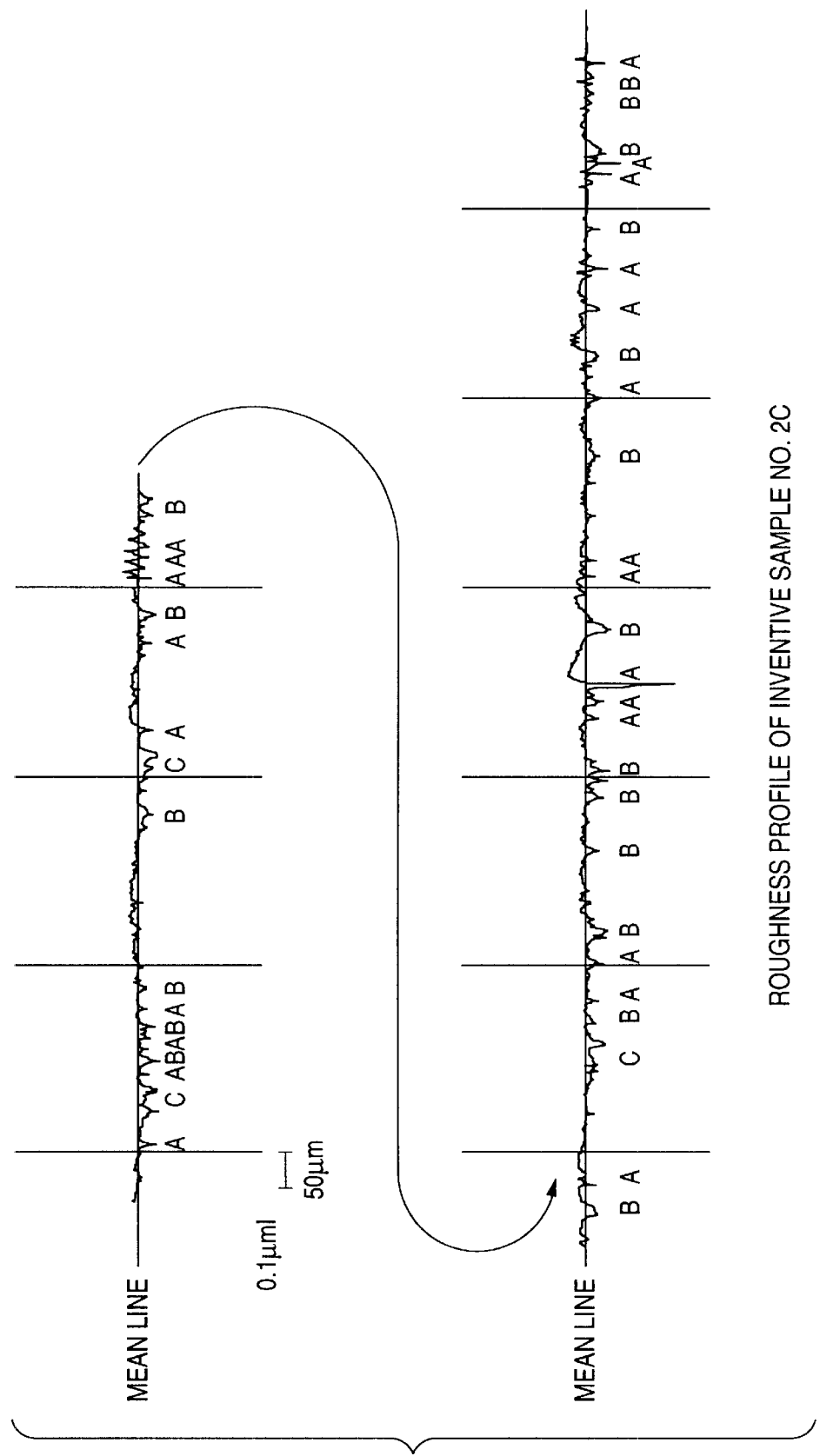
FIG. 11 is a surface roughness profile of Inventive Sample No. 2C according to the present invention.
Figure 12:
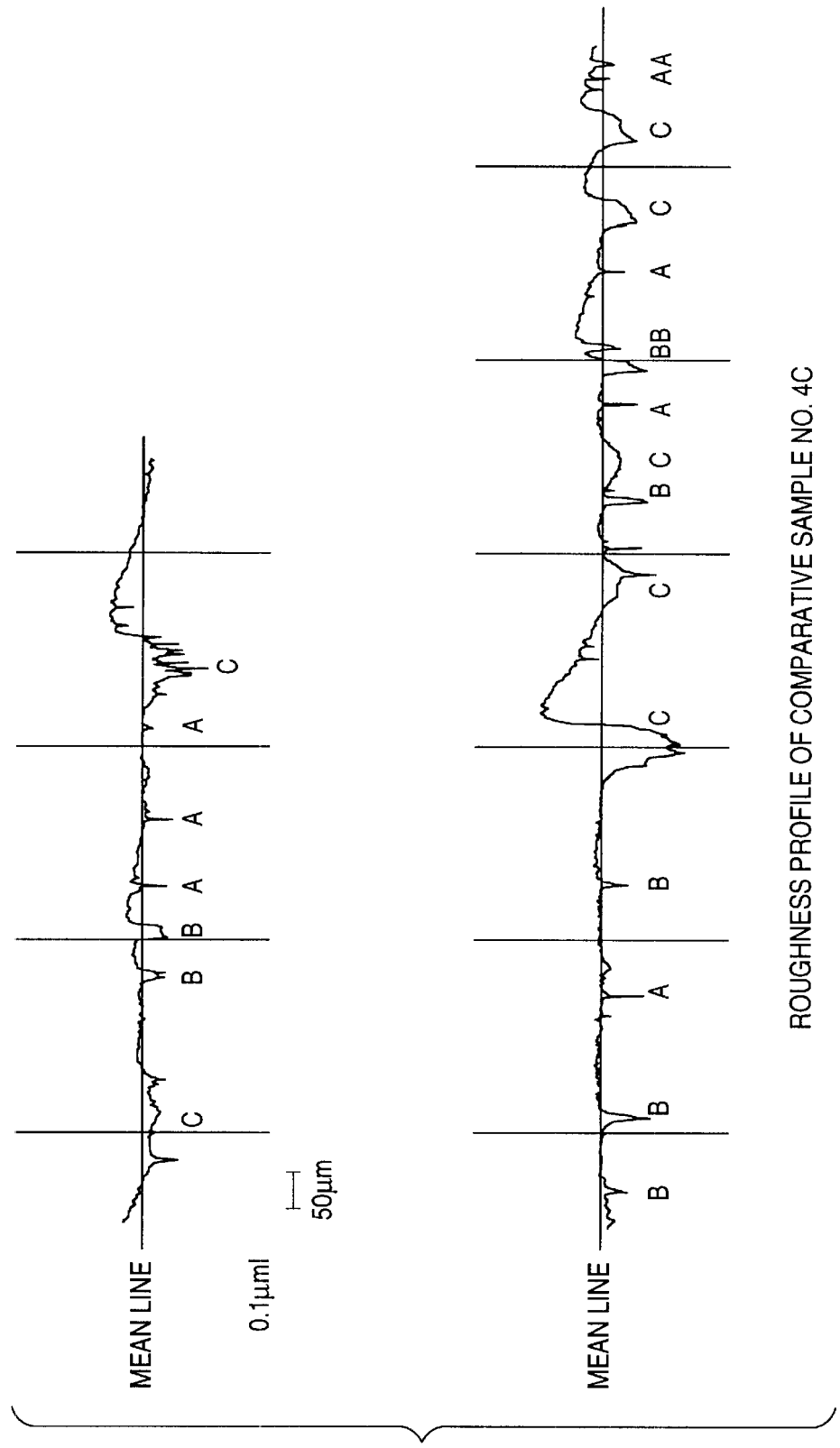
FIG. 12 is a surface roughness profile of a comparative sample.

Measuring Conditions
  Traveling speed: 0.05 mm/sec
  Vertical magnification: 5000
  Horizontal magnification: 200
  Cut-off length: 0.25 mm
  Assessment length: 2.5 mm Curvature radius of stylus: 2 μm The roughness profiles of sample Nos. 1C, 2C, and 4C are shown in FIGS. 10 to 12, respectively. As a result of roughness assessment, it is seen that the surface profile greatly varies among samples.

A mean line was drawn on the profile of sample Nos. 1C, 2C and 4C. The depressions below the mean line of the roughness profile which are formed by the curve connecting adjacent two points crossing the mean line were regarded as surface valleys. The size of each surface valley was obtained by measuring the distance between the two points (the size thus measured can be regarded as a substantial diameter of a depression), and the surface valleys were grouped by sizes into A (less than 10 μm), B (10 μm or more and less than 50 μm), and C (50 μm or more). The number of the surface valleys was counted for each group, and the ratio of each group to the total number of the surface valleys was obtained. The results obtained are shown in Table 9 below. Table 9 also shows the center-line average surface roughness (Ra; μm) specified in JIS B0601.

TABLE 9

| Sample No. | Average Particle Size (μm) | Size of Surface Valleys | | | | | | Ra (μm) |
|---|---|---|---|---|---|---|---|---|
| | | A | | B | | C | | |
| | | Number | Ratio (%) | Number | Ratio (%) | Number | Ratio (%) | |
| 1C | 1.65 | 23 | 51.1 | 19 | 42.2 | 3 | 6.7 | 0.025 |
| 2C | 1.27 | 42 | 87.5 | 6 | 12.5 | 0 | 0 | 0.014 |
| 4C | 5.52 | 8 | 34.8 | 8 | 34.8 | 7 | 30.4 | 0.058 |

As is apparent from Table 9, the surface roughness profile of sample No. 4C, which was prepared from a raw material having an average particle size greater than 1.7 μm, reveals that surface valleys of 50 μm or greater in size (diameter) constitute 30% or a larger proportion of all the surface valleys and that the center-line average surface roughness Ra is also large. These results indicate the presence of many large pores in the sintered body, which accounts for the small sinter density of sample No. 4C as shown in Table 8 (relative density: less than 94%).

On the other hand, the surface profiles of sample Nos. 1C and 2C, which were prepared from raw materials having an average particle size of 1.7 μm or smaller, show that 50% or more of the surface valleys were as small as less than 10 μm and the Ra is small. Additionally, the surface valleys are spaced relatively regularly, that is, distributed uniformly. The same observations apply to the pores inside the sintered body so that the sintered body has a large relative density of 94% or higher as shown in Table 8.

Figure 13:
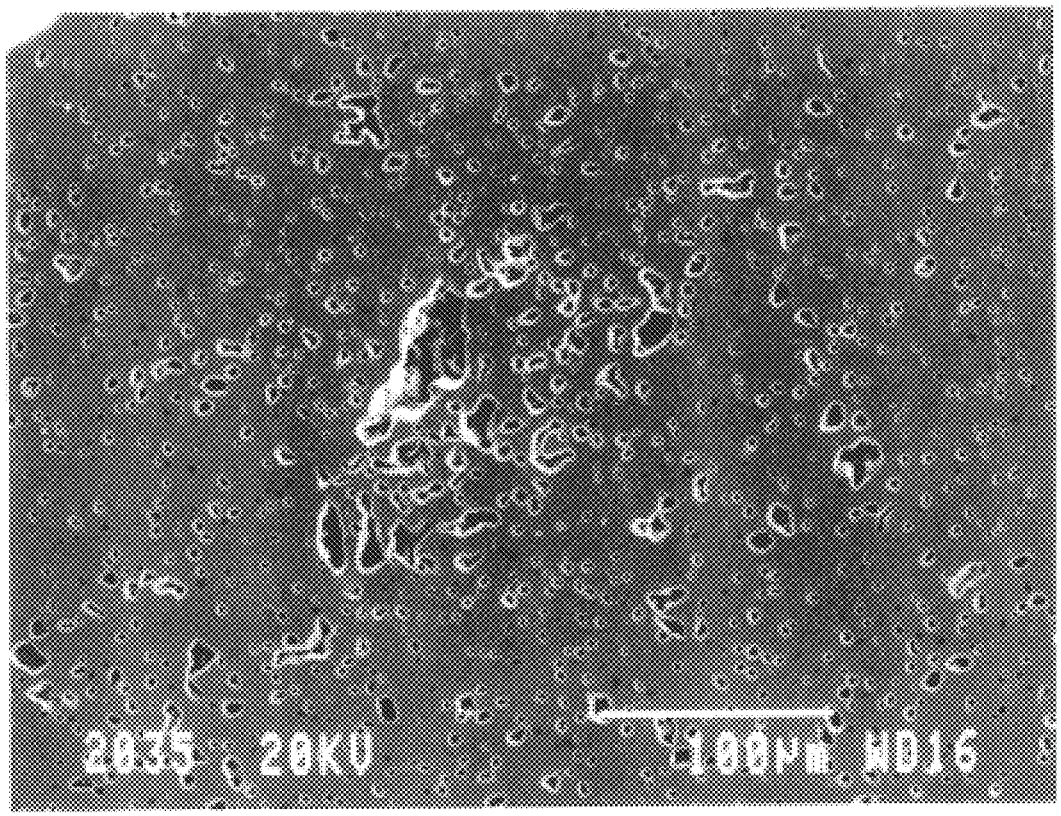
FIG. 13 is a photograph of Inventive Sample No. 1C according to the present invention taken under a scanning electron microscope.
Figure 14:
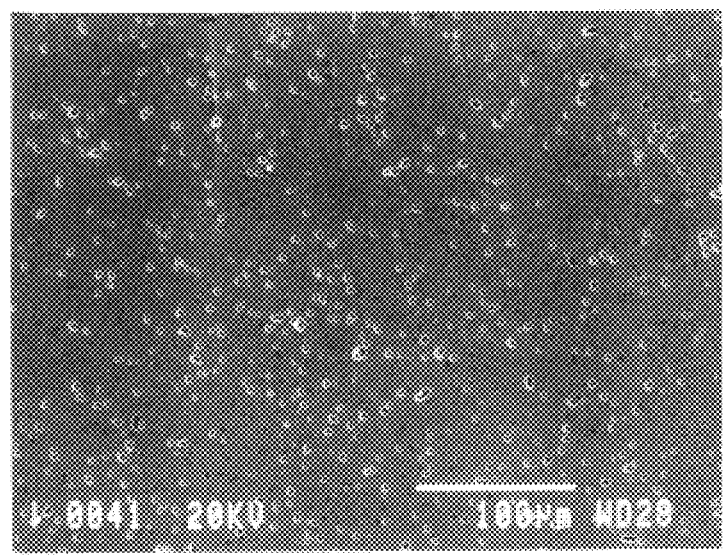
FIG. 14 is a photograph of Inventive Sample No. 2C according to the present invention taken under a scanning electron microscope.
Figure 15:
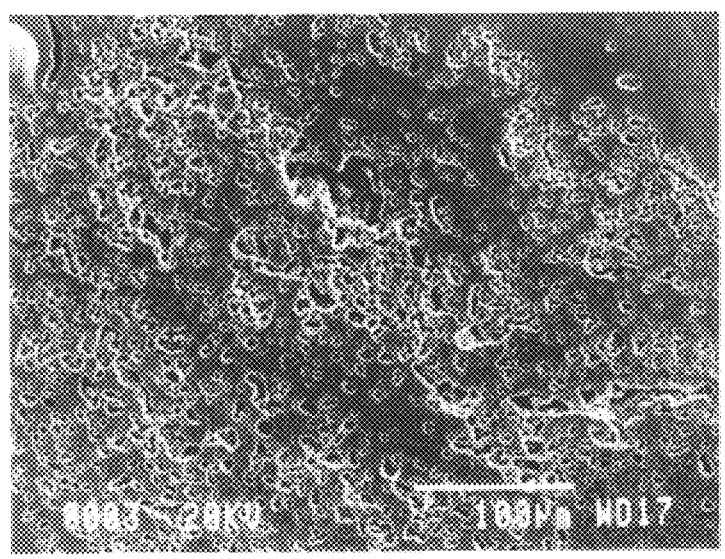
FIG. 15 is a photograph of Comparative Sample No. 4C taken under a scanning electron microscope.

The above-mentioned observations are also obtained by microscopic analysis on the mirror polished surface under a scanning electron microscope (SEM). The SEM photographs (1000×) of sample Nos. 1C, 2C, and 4C are shown in FIGS. 13 to 15, respectively. It is easily seen that the surface valleys of sample No. 4C are not uniform in size and are gathered. In contrast, the surface valleys of sample Nos. 1C and 2C are uniform in size and are uniformly distributed.

It will be easily recognized that a sintered body whose surface valleys smaller than 10 μm, as measured by roughness assessment, form 50% or more (preferably 87% or more) of the total surface valleys has the similar pore structure in the inside thereof and is therefore very dense, achieving a relative density of 94% or higher (preferably 97% or higher). According to Example in which an $LaGaO_3$-based oxide powder having an average particle size of 1.7 μm or smaller is used as a raw material, a very dense $LaGaO_3$ sintered body can be produced. The thus produced sintered body exhibits high strength, high durability, and excellent oxide ion conductivity and is extremely useful as a material of, for example, a sensor device.

The $LaGaO_3$ sintered body according to the invention is very dense as can be seen from its small surface valleys (i.e., small inside pores). It exhibits high strength, high durability, and excellent oxide ion conductivity and is extremely useful as a material of, for example, a sensor device.

The process according to the invention, being characterized by using a raw material having a controlled average particle size, easily provides an $LaGaO_3$ sintered body exhibiting the above-described superior characteristics.

What is claimed is:

1. An lanthanum gallate sintered body which comprises lanthanum, gallium, oxygen, aluminum and at least one of other elements, and has at least three crystal phases of different composition formulae.

2. An lanthanum gallate sintered body according to claim 1, wherein the molar ratio of said aluminum is 0.05 to 0.5 to the total molar amount of lanthanum, gallium and said at least one of other elements.

3. An lanthanum gallate sintered body according to claim 2, which has controlled mechanical strength and controlled electrical conductivity by varying the composition of the crystal phases by the content of aluminum.

4. An lanthanum gallate sintered body according to claim 1, which has a first crystal phase having an aluminum molar ratio of 0.06 to 0.55 to the total molar amount of lanthanum, gallium and said at least one of other elements, and a second crystal phase having an aluminum molar ratio of 0.04 to 0.6 to the total molar amount of lanthanum, gallium and said at least one of other elements.

5. An lanthanum gallate sintered body according to claim 4, wherein the first and second crystal phases have crystal phase approximate volumetric ratios to the total crystal phases of 0.55 to 0.9, and 0.4 or less, respectively.

6. An lanthanum gallate sintered body according to claim 1, which has an four-point bending strength of 250 MPa or higher as measured in accordance with JIS R1601.

7. A sensor device comprising an oxide ion-conducting solid electrolyte comprising the lanthanum gallate sintered body according to claim 1 and an electrode formed on said solid electrolyte.

8. A sensor device according to claim 7, wherein said electrode contains at least one of a mixed oxide and a metal oxide.

9. A sensor device according to claim 8, wherein said metal oxide is at least one member selected from the group consisting of $MnO_2$, $MoO_3$, $Nd_2O_3$, $Fe_2O_3$, $WO_3$, $Nb_2O_5$, $Ta_2O_5$, $TiO_2$, $In_2O_3$, $IrO_2$, $Rh_2O_3$, CuO and $CuO_2$, and said mixed oxide is an $LaGaO_3$ mixed oxide.

10. A sensor device according to claim 7, wherein said electrode comprises at least one metal selected from the group consisting of Pt, Au, Pd, Ir, Rh, In, Ag, Tl and Cu.

11. An lanthanum gallate sintered body according to claim 1, wherein the lanthanum gallate sintered body has a surface roughness profile determined according to JIS B0601 showing that the proportion of concave portions below the mean line having a size less then 10 μm, excluding 0 μm, in all the concave portions below the mean line is 50% or more in number, the size being the distance between two adjacent intersections of the mean line with the profile forming one or more concave portions below the mean line.

12. An lanthanum gallate sintered body according to claim 11, which has a density of 94% or more of the theoretical density for the sintered body.

13. An lanthanum gallate sintered body according to claim 11, wherein said proportion of concave portions below the mean line having a size less than 10 µm in all the convex portions below the mean line is 87% or more in number.

14. An lanthanum gallate sintered body according to claim 13, which has a density of 97% or more of the theoretical density for the sintered body.

15. An lanthanum gallate sintered body according to claim 11, which is produced by using an $LaGaO_3$-based powder having an average particle size of 1.7 µm or smaller as a raw material.

16. An lanthanum gallate sintered body according to claim 15, which has a density of 94% or more of the theoretical density for the sintered body.

17. An lanthanum gallate sintered body according to claim 16, which has a density of 97% or more of the theoretical density for the sintered body.

18. A process for producing an lanthanum gallate sintered body according to claim 11, which comprises starting with an $LaGaO_3$-based powder having an average particle size of 1.7 µm or smaller.

* * * * *